United States Patent [19]

Anderson

[11] 4,004,009

[45] Jan. 18, 1977

[54] ANTIHYPERTENSIVE ARYL PYRAZOLO[4,3-c]PYRIDAZINONES

[75] Inventor: Paul L. Anderson, Dover, N.J.

[73] Assignee: Sandoz, Inc., E. Hanover, N.J.

[22] Filed: July 31, 1975

[21] Appl. No.: 600,885

[52] U.S. Cl. .......................... 424/250; 260/250 A; 260/250 AC
[51] Int. Cl.² ................ A61K 31/50; C07D 487/04
[58] Field of Search .............. 424/250; 260/250 AC

[56] References Cited

UNITED STATES PATENTS 3,940,248  2/1976  Yamaguchi ................. 260/250 AC

OTHER PUBLICATIONS

Khadem et al., Chem. Abs. 78, 4200y (1973).

*Primary Examiner*—R. Gallagher
*Assistant Examiner*—Mark L. Berch
*Attorney, Agent, or Firm*—Gerald D. Sharkin; Richard E. Vila; Frederick H. Weinfeldt

[57] ABSTRACT

The compounds are aryl-pyridazinone derivatives, e.g., 1-methyl-5-(2'-fluoro-5'-trifluoromethylphenyl)-1H-pyrazolo [4,3-c]pyridazin-6(5H)-one. They are useful as antihypertensives and are prepared by treating a hydrazinopyridazinone with a dialkylamino dialkylacetal.

15 Claims, No Drawings

ANTIHYPERTENSIVE ARYL PYRAZOLO[4,3-c]PYRIDAZINONES

This invention relates to organic compounds and, more particularly, to mono-cyclic and bicyclic aryl-pyridazinones and pharmaceutically-acceptable acid addition salts thereof, as well as to pharmaceutical compositions containing such compounds, and the pharmaceutical use of such compounds.

The compounds of this invention are Compounds I, which class consists of compound Ia:

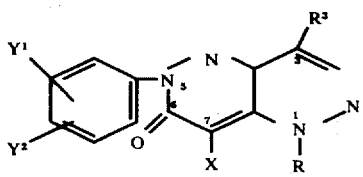

and Compounds Ib:

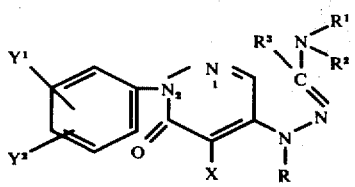

wherein

X is a hydrogen atom, or halo having an atomic weight of from about 19 to 36, i.e., fluoro or chloro;

$Y^1$ and $Y^2$ are the same or different and are selected from the group consisting of a hydrogen atom, halo having an atomic weight of from about 19 to 80, i.e., fluoro, chloro or bromo, trifluoromethyl, alkyl having from 1 to 4 carbon atoms and alkoxy having from 1 to 4 carbon atoms, providing that when both $Y^1$ and $Y^2$ are trifluoromethyl or branched alkyl they are not on adjacent carbon atoms;

R is a hydrogen atom or alkyl having from 1 to 3 carbon atoms, preferably methyl; each of $R^1$ and $R^2$ is alkyl having from 1 to 3 carbon atoms, which may be the same or different; and $R^3$ is a hydrogen atom or alkyl having from 1 to 4 carbon atoms; and pharmaceutically acceptable acid addition salts of Compounds Ia and Ib.

With reference to the definitions of alkyl and alkoxy above, it is understood that the alkyl portion may be branched or unbranched.

The above-described Compounds I may be prepared by reacting, under essentially anhydrous conditions, and in an inert solvent, a compound of the formula II

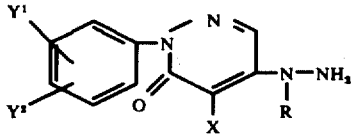

in which $Y^1$, $Y^2$, X and R are as defined above, with an amino compound of the formula III:

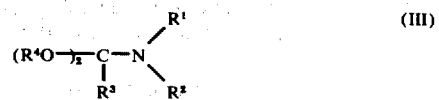

in which $R^1$, $R^2$ and $R^3$ are as defined above, and $R^4$ is lower alkyl, e.g., having from 1 to 3 carbon atoms, preferably methyl (process a).

Process a) is carried out in the presence of an inert solvent having a relatively high boiling point, preferably dimethylformamide, at an elevated temperature, e.g., from about 110° C. to 150° C. Essentially anhydrous conditions used are achieved by means conventionally practiced where it is desired to essentially exclude moisture, e.g., by the use of absolute (dry) reaction medium and reagents, employing moisture-free apparatus and excluding moisture-laden air, and preferably in an atmosphere of dry nitrogen. Preferably compound III is used in excess, and it is also preferred to add additional compound III after the reaction has been carried out for a period of time. Reaction times are generally from about 12 to 75 hours. It is convenient to monitor the progress of the reaction by thin layer chromatography; a compound Ia and its corresponding compound Ib being obtained as co-products.

Compounds II are known and may be prepared as described in the literature, Belgian Pat. No. 791,098, or where not known may be prepared by methods analogous to methods described in the literature for the preparation of those compounds which are known. Compounds II may be conveniently obtained by reaction of a compound IV:

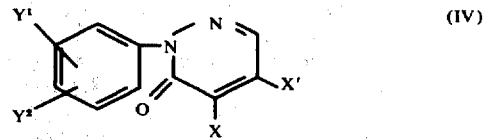

in which $Y^1$, $Y^2$ and X are as defined above, and X' is a halogen having an atomic weight of from about 35 to 80, i.e., chloro or bromo, preferably chloro, with a hydrazine of the formula V:

in which R is as defined above, in the presence of an inert solvent, e.g., a lower alkanol, e.g., methanol at from about 20° to 150° C., preferably from about 45° to 65° C.

Other above-described reactants and reagents, e.g., Compounds III, IV and V are known, and are obtainable by methods described in the literature; some being commercially available, or where not known, may be prepared by methods analogous to those described in the literature for the preparation of those compounds which are known.

The above-described reaction products may be recovered and refined by conventional techniques, e.g., by crystallization, distillation or chromatographic techniques, e.g., thin-layer or column chromatography, as is appropriate.

Process a) described above may conveniently be represented by Reaction Scheme A below, in which $Y^1$, $Y^2$, R, $R^1$, $R^2$, $R^3$, $R^4$ and X are as defined above.

REACTION SCHEME A

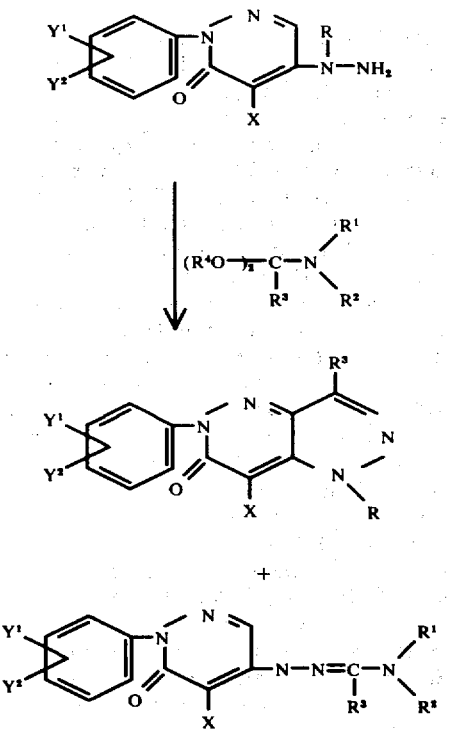

The compounds of formula I are useful because they possess pharmacological activity in animals. In particular, the compounds I are useful as anti-hypertensive agents, as indicated by standard anti-hypertensive tests, e.g., a test in which five male albino spontaneously hypertensive rats (weighing about 240 to 320 grams) are placed into individual restraining cages. A pneumatic pulse transducer is affixed to the tail of each animal so that the sensor is directly in contact with the caudal artery. Blood pressure is monitored via a Sanborn Model 296 polygraph, and heart rate calculated from the tracing. Two control measurements are made prior to drug administration. Additional measurements are made after drug administration every 30 minutes for the first 2 hours and every 60 minutes for the next 3 hours. The test compound is given orally as a suspension in 1.5% carboxymethylcellulose (CMC) in a volume of 2 cc per kilogram body weight. The mean percent change from pre-drug condition is calculated for the five drug-treated animals. Significance is determined for difference between this group and an ongoing control group of 20 CMC-treated animals by comparison of the mean percent change ± standard deviation values of the two groups.

For such usage, the compounds (I) may be combined with a pharmaceutically-acceptable carrier or adjuvant and may be administered orally or parenterally as such or admixed with conventional pharmaceutical carriers. They may be administered in such forms as tablets, dispersible powders, granules, capsules, syrups and elixirs and parenterally as solutions, suspensions, dispersions, emulsions and the like, e.g., a sterile injectable aqueous formulation. The dosage will vary depending upon the mode of administration utilized and the particular compound employed, etc.

The compounds of formula (I) may be similarly administered in the form of their non-toxic pharmaceutically-acceptable salts. Such salts possess the same order of activity as the free base, and are readily prepared by reacting the base with an appropriate pharmaceutically-acceptable acid, and accordingly, are included within the scope of this invention. Representative of such salts are the mineral acid salts, such as the hydrochloride, hydrobromide, sulfate, phosphate and the like and the organic acid salts such as succinate, benzoate, acetate, p-toluenesulfonate, benzenesulfonate and the like.

The anti-hypertensive effective dosage of compounds (I) employed in the treatment of hypertension will vary depending on the particular compound employed and the severity of the condition being treated. However, in general, satisfactory results are obtained when the compounds of formula (I) are orally administered at a daily dosage of from about 1 to about 100 milligrams per kilogram of animal body weight, preferably given in divided doses two to four times per day, or in sustained release form. For most large mammals, the total daily dosage is from about 75 milligrams to about 1500 milligrams. Dosage forms suitable for internal use comprise from about 20 to about 750 milligrams of active compound in intimate admixture with a solid or liquid pharmaceutically-acceptable carrier of diluent. In general, oral administration is preferred. Solid compositions, e.g., capsules and tablets, are most preferred.

A representative formulation suitable for oral administration 2 to 4 times a day for the treatment of hypertension is a capsule prepared by standard encapsulating techniques which contain the following:

| Ingredients | Weight (mg) |
| --- | --- |
| 1-methyl-5-(2'-fluoro-5'-trifluoromethylphenyl)-1H-pyrazolo[4,3-c]pyridazin-6-(5H)-one | 100 |
| inert solid diluent (starch, lactose, kaolin) | 200 |

In the following examples, which are illustrative of the invention, temperatures are in degrees centigrade, and room temperature is 20° to 30° C. unless indicated otherwise.

Preferred compounds I are those compounds of the subclass Ia. Compounds I in which R is methyl are also preferred.

PREPARATION 1

4-chloro-5-(1-methylhydrazino)-2-(3'-trifluoromethylphenyl)-3-(2H)-pyridazinone

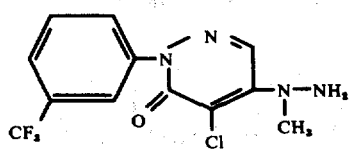

This example illustrates the preparation of starting materials (Compounds II) for the process of this invention, but is not part of the invention.

To a solution consisting of 15.5 grams of 4,5-dichloro-2-(3-trifluoromethylphenyl)-3(2H)-pyridazinone in 120 grams of methanol is added 9.2 grams methylhydrazine. The reaction mixture is heated to 45° C. for 3 hours, cooled and poured onto 250 grams of water. The resulting precipitate is separated by filtration, washed with water and dried. The solid is crystallized from benzene to yield 4-chloro-5-(1-methylhydrazino)-2-(3′-trifluoromethylphenyl)-3-(2H)-pyridazinone. (m.p. 140° to 141° C. with decomposition).

When the above reaction is carried out using in place of the 4,5-dichloro-2-(3-trifluoromethylphenyl)-3-(2H)-pyridazinone, an approximately equivalent amount of:
  a. 5-chloro-2- (2-fluoro-5-trifluoromethylphenyl)-3(2H)-pyridazinone;
  b. 4,5-dichloro-2-(2-fluoro-5-trifluoromethylphenyl)-3(2H)-pyridazinone; or
  c. 5-chloro-2-(3-trifluoromethylphenyl)-3(2H)-pyridazinone. there is accordingly obtained:
  a. 2-(2′-fluoro-5′-trifluoromethylphenyl)-5-(1-methylhydrazino-3(2H)-pyridazinone;
  b. 4-chloro-2-(2′-fluoro-5′-trifluoromethylphenyl)-5-(1-methylhydrazino)-3(2H)-pyridazinone (m.p. 128°–130° C.); and
  c. 5-(1-methylhydrazino)-2-(3′-trifluoromethylphenyl)-3(2H)-pyridazinone.

EXAMPLE 1

1-methyl-5-(2′-fluoro-5′-trifluoromethylphenyl)-1H-pyrazolo[4,3-c]pyridazin-6-(5H)-one

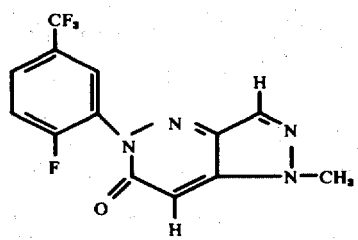

In 250 ml. of absolute dimethylformamide (dried over molecular sieves) under a nitrogen atmosphere, are dissolved 14.5 grams of 2-(2-fluoro-5-trifluoromethylphenyl)-5-(1-methylhydrazino)-3(2H)-pyridazinone. To this solution are added 11.4 grams of N,N-dimethylformamide dimethyl acetal and the solution is heated at 110°–120° C. overnight. The progress of the reaction is followed by thin layer chromatography. An additional 6.0 grams of N,N-dimethylformamide dimethyl acetal is added with continued heating to complete the reaction (about 20 hours). The reaction mixture is then evaporated to dryness in vacuo and then column chromatographed on silica gel, eluting with a mixture of benzene-chloroform (50/50), to obtain the title product. (m.p. 190°–195° C.).

The wet chromatographic column is retained for use in Example 2, below.

Repeating the procedure of this example, but using in place of the N,N-dimethylformamide dimethyl acetal, an approximately equivalent amount of N,N-dimethylacetamide dimethyl acetal, there is, accordingly, obtained 1,3-dimethyl-5-(2′-fluoro-5′-trifluoromethylphenyl)-1H-pyrazolo [4,3-c]pyrazin-6-(5H)-one.

EXAMPLE 2

5-(2-dimethylaminomethylidene-1-methylhydrazino)-2-(2′-fluoro-5′-trifluoromethylphenyl)-3(2H)-pyridazinone

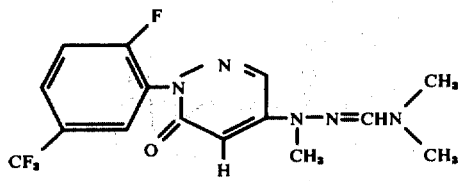

The chromatographic column used in Example 1, is subsequently eluted with chloroform to obtain the title product, m.p. 134°–137° C.

EXAMPLE 3

7-chloro-1-methyl-5-(3′-trifluoromethylphenyl)-1H-pyrazolo[4,3-c]pyridazin-6-(5H)-one

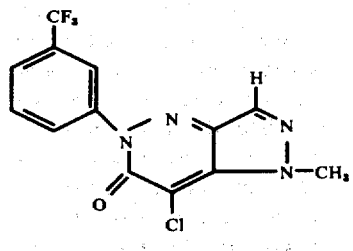

In 100 ml. of absolute dimethylformamide (dried over molecular sieves) under a nitrogen atmosphere, are dissolved 9.6 grams of 4-chloro-5-(1-methylhydrazino)-2-(3′-trifluoromethylphenyl)-3(2H)-pyridazinone. To this solution are added 3.9 grams of N,N-dimethylformamide dimethyl acetal and the solution is heated at 110°–120° C. overnight. The progress of the reaction is followed by thin layer chromatography. An additional 3.9 grams of N,N-dimethylformamide dimethyl acetal are added with continued heating to complete the reaction (about 20 hours). The reaction mixture is then evaporated to dryness in vacuo and then column chromatographed on silica gel, eluting with a mixture of benzene-chloroform (50/50), to obtain the title product. (m.p. 156°–158° C.).

The wet chromatographic column is retained for use in Example 4, below.

EXAMPLE 4

4-chloro-5-(2-dimethylaminomethylidene-1-methylhydrazino)-2-(3′-trifluoromethylphenyl)-3(2H)-pyridazinone

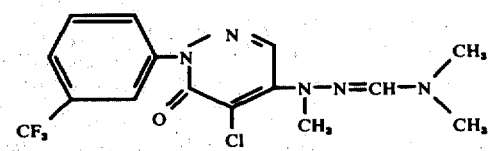

The chromatographic column used in Example 3 is subsequently eluted with chloroform to obtain the title product, m.p. 80°–85° C.

EXAMPLE 5

7-chloro-1-methyl-5-(2'-fluoro-5'-trifluoromethylphenyl)-1H-pyrazolo[4,3-c]pyridazin-6-(5H)-one

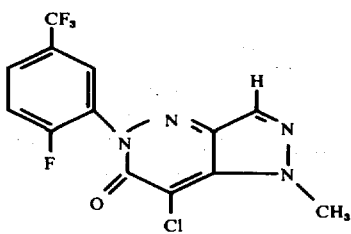

In 300 ml. of absolute dimethylformamide (dried over molecular sieves) under a nitrogen atmosphere, are dissolved 19.8 grams of 4-chloro-2-(2'-fluoro-5°-trifluoromethylphenyl)-5-(1-methylhydrazino-3-(2H)-pyridazinone. To this solution are added 11.9 grams of N,N-dimethylformamide dimethyl acetal and the solution is heated at 110°–120° C. for 48 hours. The progress of the reaction is followed by thin layer chromatography. An additional 9.0 grams of N,N-dimethylformamide dimethyl acetal are added with continued heating to complete the reaction (about 20 hours more). The reaction mixture is then evaporated to dryness in vacuo and column chromatographed on silica gel, eluting with a mixture of benzene-chloroform (50/50), to obtain the title product. (m.p. 177°–182° C.).

EXAMPLE 6

1-methyl-5-(3'-trifluoromethylphenyl)-1H-pyrazolo[4,3-c]pyridazin-6-(5H)-one

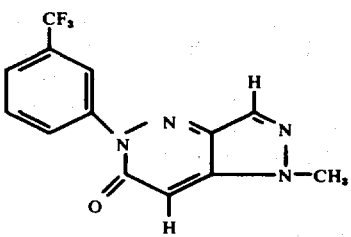

In 225 ml. of absolute dimethylformamide (dried over molecular sieves) under a nitrogen atmosphere are dissolved 8.5 grams of 5-(1-methylhydrazino)-2-(3'-trifluoromethylphenyl)-3(2H)-pyridazinone. To this solution are added 7.1 grams of N,N-dimethylformamide dimethyl acetal and the solution is refluxed for 72 hours. The reaction is followed by thin layer chromatography The reaction mixture is then evaporated to dryness in vacuo and column chromatographed on silica gel, eluting with a mixture of benzene-chloroform (50/50), to obtain the crude title product which is then refined by preparative chromatography on a silica gel plate, eluting with chloroform to give crystalline title product, which is then washed with diethyl ether, m.p. 160°–163° C.

The wet chromatographic column used in this example is retained for use in Example 7, below.

EXAMPLE 7

5-(2-dimethylaminomethylidene-1-methylhydrazino)-2-(3'-trifluoromethylphenyl)-3(2H)-pyridazinone

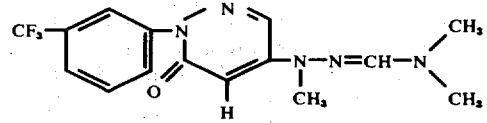

The chromatographic column used in Example 6, above, is subsequently eluted with chloroform to obtain the title product, m.p. 79°–85° C.

What is claimed is:

1. A compound which is a pyridazinone of the formula:

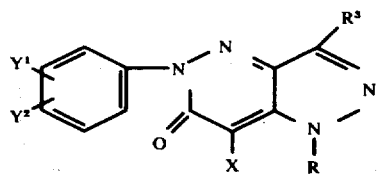

wherein
X is a hydrogen atom, fluoro or chloro;
$Y^1$ and $Y^2$ are the same or different and are selected from the group consisting of a hydrogen atom, alkyl having from 1 to 4 carbon atoms, fluoro, chloro, bromo, trifluoromethyl, and alkoxy having from 1 to 4 carbon atoms, provided that when both $Y^1$ and $Y^2$ are trifluoromethyl or branched alkyl, they are not on adjacent carbon atoms;
R is a hydrogen atom or alkyl having from 1 to 3 carbon atoms; and
$R^3$ is a hydrogen atom or alkyl having from 1 to 4 carbon atoms; or a pharmaceutically acceptable acid addition salt thereof.

2. A compound of claim 1 in which R is a hydrogen atom.

3. A compound of claim 1 in which R is alkyl.

4. A compound of claim 3 in which R is methyl.

5. A compound of claim 4 in which $Y^1$ is meta-trifluoromethyl.

6. The compound of claim 5 which is 1-methyl-5-(2'-fluoro-5'-trifluoromethylphenyl)-1H-pyrazolo[4,3-c]pyridazin-6-(5H) -one.

7. The compound of claim 5 which is 7-chloro-1-methyl-5-(3'-trifluoromethylphenyl)-1H-pyrazolo[4,3-c]pyridazin-6-(5H)-one.

8. The compound of claim 5 which is 7-chloro-1-methyl-5-(2'-fluoro-5'-trifluoromethylphenyl) -1H-pyrazolo [4,3-c]pyridazin-6-(5H)-one.

9. The compound of claim 5 which is 1-methyl-5-(3'-trifluoromethylphenyl)-1H-pyrazolo[4,3-c]pyridazin-6-(5H)-one.

10. A pharmaceutical composition useful for treating hypertension in a mammal comprising a compound of claim 1 in hypertension-reducing effective amount and a non-toxic pharmaceutically acceptable carrier therefor.

11. A composition of claim 10 in which the compound is present in an amount of from about 20 to 750 milligrams.

12. A composition of claim 10 which is a solid composition.

13. A method of treating hypertension in a mammal in need of such treatment comprising internally administering a compound of claim 1, in an amount effective in reducing hypertension, to said mammal.

14. A method of claim 13 in which the compound is administered in an amount of from about 75 to 1500 milligrams daily.

15. A method of claim 13 in which the mode of administration is oral administration.

* * * * *